United States Patent [19]

Coury et al.

[11] Patent Number: 5,133,422
[45] Date of Patent: Jul. 28, 1992

[54] RADIO FREQUENCY GLOW DISCHARGE SURFACE TREATMENT OF SILICONE TUBING USED AS COVERING FOR ELECTRICAL LEADS TO IMPROVE SLIP PROPERTIES THEREOF

[75] Inventors: Arthur J. Coury, St. Paul, Minn.; Patrick T. Cahalan, Stein, Netherlands; Edward D. Di Domenico, Jr., Anoka, Minn.; Kenneth W. Keeney, Forest Lake, Minn.; John M. Swoyer, Coon Rapids, Minn.

[73] Assignee: Medtronic, Inc., Minneapolis, Minn.

[21] Appl. No.: 754,326

[22] Filed: Sep. 4, 1991

Related U.S. Application Data

[63] Continuation of Ser. No. 457,019, Dec. 26, 1989, abandoned.

[51] Int. Cl.$^5$ .............................................. A61N 1/04
[52] U.S. Cl. ................................................ 128/784
[58] Field of Search ............... 128/784, 786; 604/20, 604/21, 172, 265; 204/165, 168, 169

[56] References Cited

U.S. PATENT DOCUMENTS 4,332,259  6/1982  McCorkle, Jr. ..................... 128/786
4,508,606  4/1985  Andrade et al. ..................... 204/165

OTHER PUBLICATIONS

"Gas-Discharge Techniques for Biomaterial Modification" by Gombotz and Hoffman, CRC Critical Reviews in Biocompatibility, vol. 4, Issue 1 (1987), pp. 1-42.
"Surface Modification and Evaluation of Some Commonly Used Catheter Materials. I. Surface Properties" by Triolo and Andrade, Journal of Biomedical Materials Research, vol. 17, pp. 129-247 (1983).
"Surface Modification and Characterization of Some Commonly Used Catheter Materials, II. Friction Characterization" by Triolo and Andrade, Journal of Biomedical Materials Research, vol. 17, pp. 149-165 (1983).

Primary Examiner—William F. Kamm
Attorney, Agent, or Firm—Vidas & Arrett

[57] ABSTRACT

Improved electrical leads provided by the surface treatment of silicone rubber tubing covering on implantable pulse generator, or IPG leads and the like by exposure of the silicone rubber to radio frequency glow discharge in a polymer forming or non-polymer forming gas at reduced pressure whereby improved slip properties are provided and binding between two or more of the leads in contact with each other is minimized.

17 Claims, 4 Drawing Sheets

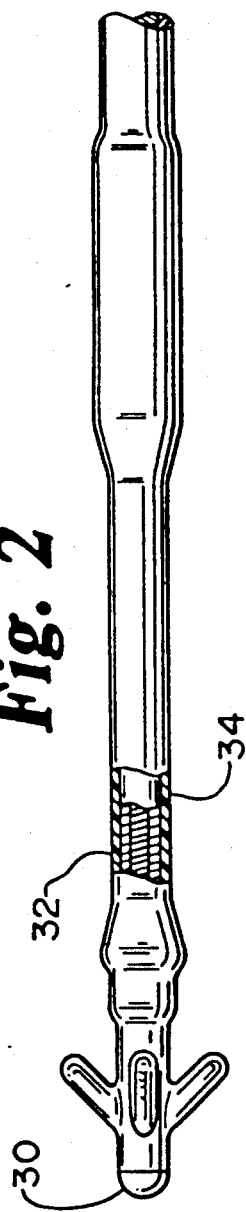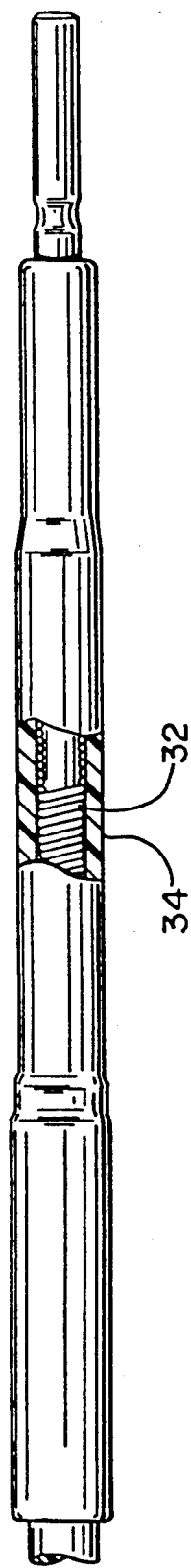

RADIO FREQUENCY GLOW DISCHARGE SURFACE TREATMENT OF SILICONE TUBING USED AS COVERING FOR ELECTRICAL LEADS TO IMPROVE SLIP PROPERTIES THEREOF

This is a continuation of copending application Ser. No. 07/457,019 filed on Dec. 26, 1989 now abandoned.

BACKGROUND OF THE INVENTION

In general, this invention relates to improved electrical leads. More particularly it relates to improved leads for implantable pulse generators (IPG's) such as heart pacemakers. Heart pacemakers may have one or more leads incorporating this invention. Such implantable medical devices require elongate electrical leads which attach to sites in the body for electrical contact therewith. The surfaces of the leads often contact each other and rub against each other. In the case of transvenous heart pacemakers which are implanted in the chest, a pair of leads may extend through a blood vessel into the heart for interior attachment thereto. The two leads extend through a common vessel for some portion of their entry path and rub against each other in various surface areas.

It has become common practice to include silicone rubber as a surface covering for such leads because it is biocompatible and biostable. It is particularly common to utilize silicone rubber tubing for this purpose. A continuing problem with the use of silicone rubber has been the binding which occurs when these outer coverings rub against each other. Such binding is often referred to as "surface blocking" or simply "blocking" Implantation side-by-side thus has been found to give rise to sticking and even dislodgment of the leads.

Various surface coatings have been tried in an effort to reduce "blocking" and improve the "slip" of silicone rubber. However, such coatings have been found to have too short a lifetime or to lack biocompatibility and/or biostability.

It is a specific object of this invention to provide silicone rubber with improved surface properties in this regard and particularly to provide silicone rubber tubing and coverings for leads and in combination with leads which exhibit permanent and improved "blocking" and "slip."

SUMMARY OF THE INVENTION

The objects of the invention are attained by providing leads with silicone rubber coverings, especially tubing, which have been surface treated by radio frequency glow discharge. Such treatment has been found to permanently improve the surface characteristics of silicone rubber coverings for leads with respect to the aforementioned problems.

BRIEF DESCRIPTION OF THE DRAWINGS

FIGS. 2 and 3 show the structure of a typical IPG lead, distal and proximal end portions respectively;

DESCRIPTION OF THE PREFERRED EMBODIMENTS

Figure 1:
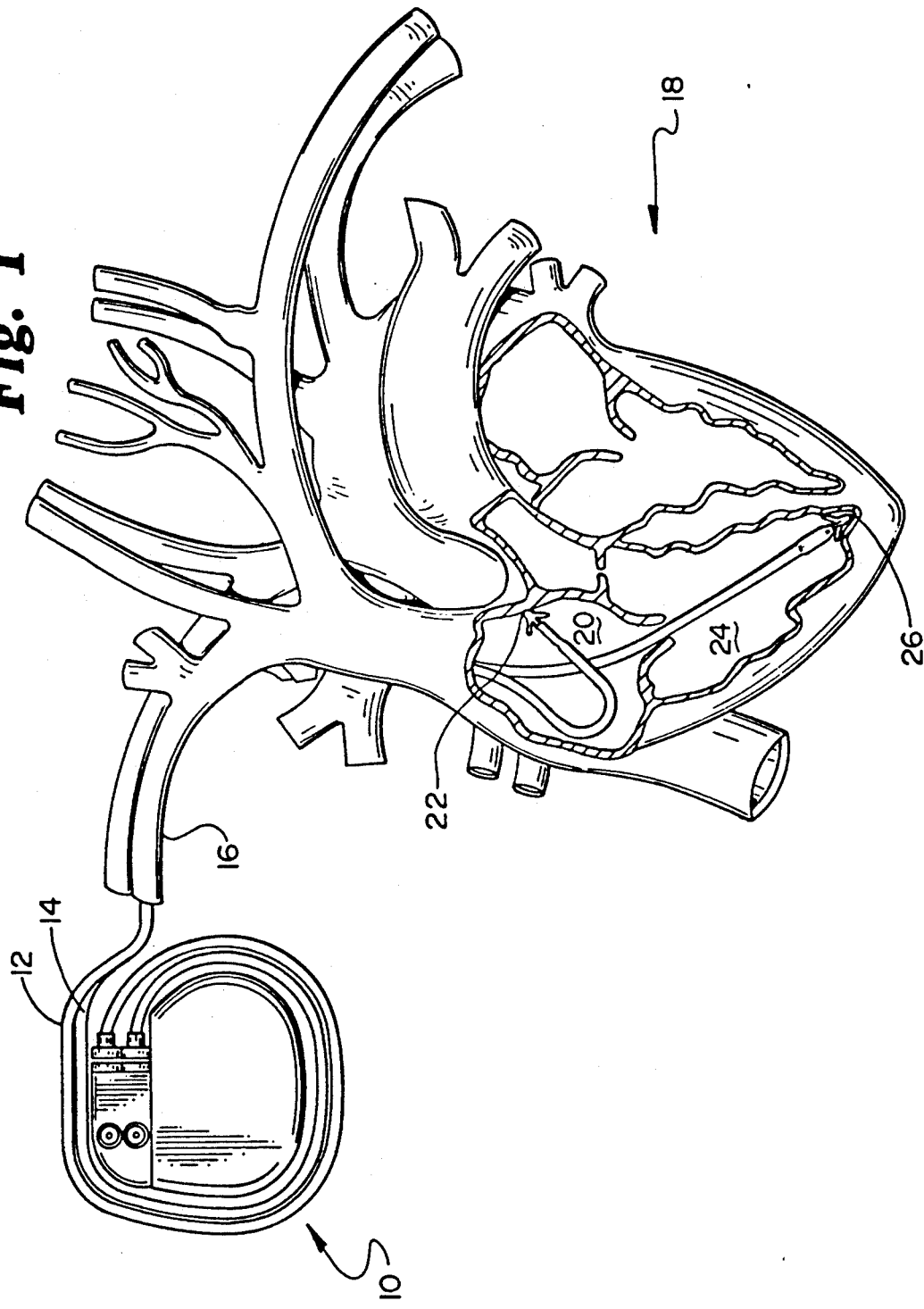
FIG. 1 represents in schematic form the implantation of a heart pacemaker IPG and a pair of electrical leads in a human heart.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Referring to FIG. 1, an implanted heart pacemaker IPG 10 is shown having two electrical leads, atrial lead 12 and ventricular lead 14, extending through a common vessel, such as the R. Brachiocephalis vein 16, of a human heart generally indicated at 18. The paired leads extend into the right atrium 20 of the heart where lead 12 is attached to a site 22. Lead 14 extends through atrium 20 and into right ventricle 24 where it likewise is attached to a site 26. As can be readily seen, leads 12 and 14 during implantation through vessel 16 undergo a certain amount of mutual rubbing together over portions of their length. Likewise, after implantation, movement of the heart and general movement of the patient causes a certain amount of mutual rubbing contact between the leads. The resultant sticking together and even dislodgment as aforementioned are obviated by the improvement of this invention.

As already mentioned, the improvement herein focuses on the outer surface of the leads, which is typically comprised of a silicone rubber covering. A typical lead is shown in FIG. 2 and in FIG. 3. Such a lead will include among other things at its distal portion as shown in FIG. 2 an electrode assembly 30, an elongate conductive coil 32 and an outer elongate covering 34 over its length comprised of silicone rubber tubing or the like. Likewise, the proximal portion as shown in FIG. 3 will also include the same continuing elements of conductive coil 32 and silicone rubber tubing 34.

The surface treatment provided for the silicone rubber tubing 34 is preferably applied to the tubing before it is placed over the lead structure. It may of course be applied at other stages in the lead manufacturing process, particularly if silicone rubber is used in a form other than tubing.

The theory and practice of radio frequency (RF) gas discharge is explained in great detail in 1) "Gas-Discharge Techniques For Biomaterial Modification" by Gombatz and Hoffman, *CRC Critical Reviews in Biocompatibility*, Vol. 4, Issue 1 (1987), pp 1–42; 2) "Surface Modification and Evaluation of Some Commonly Used Catheter Materials. I. Surface Properties" by Trials and Andrade, *Journal of Biomedical Materials Research*, Vol 17, 129–147 (1983), and 3) "Surface Modification and Evaluation of Some Commonly Used Catheter Materials, II. Friction Characterized" also by Trialo and Andrade, *Journal of Biomedical Materials Research*, Vol. 17, 149–165 (1983), and need not be described again herein. All of the foregoing is incorporated herein by reference. Suffice it to say here that the gas discharge process or radio frequency flow discharge (RFGD) as contemplated herein gives rise to a plasma of various ionized and other charged species which interact with surfaces exposed thereto, such as silicone rubber surfaces, to alter same by reaction therewith.

Figure 4:
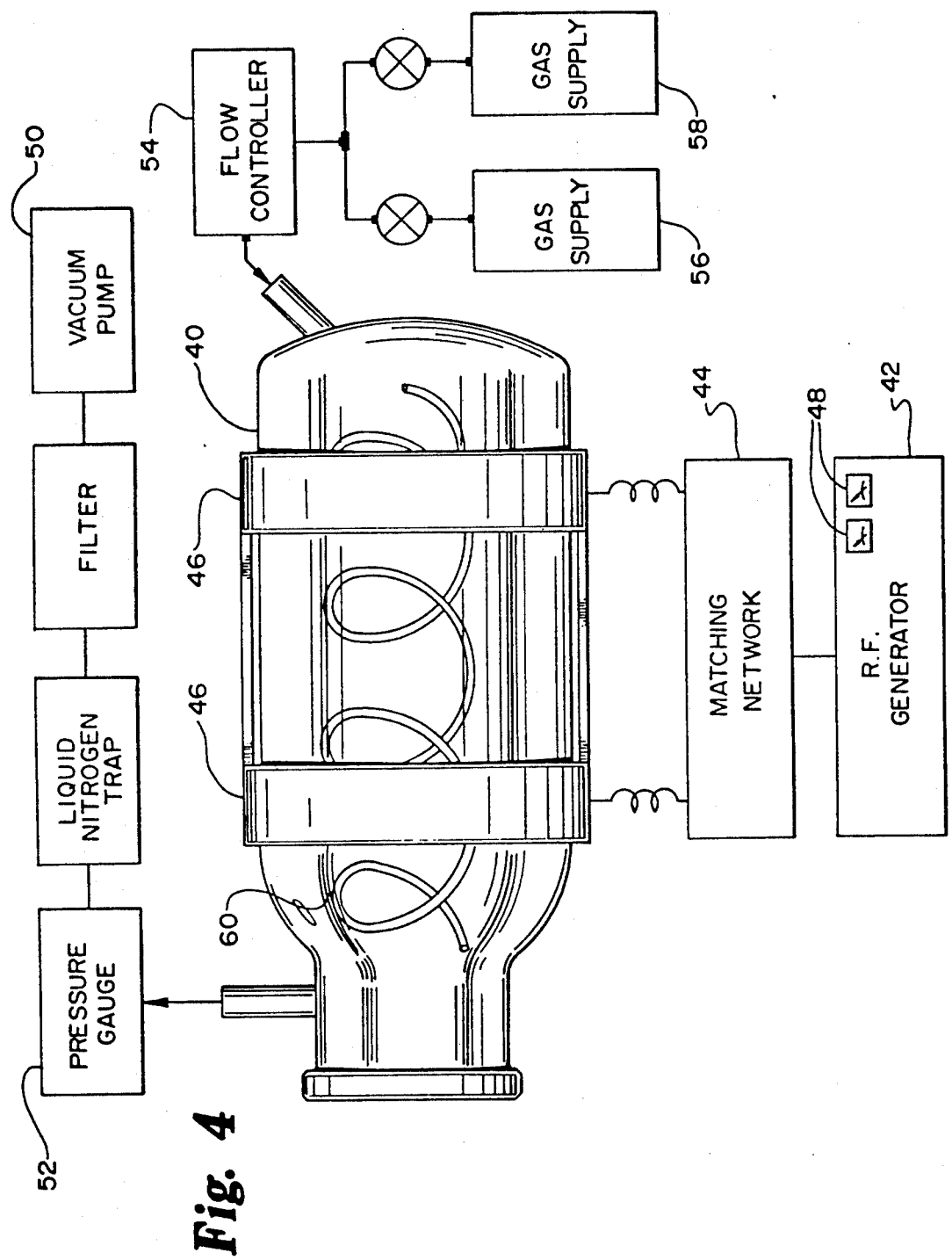
FIG. 4 shows schematically an apparatus for carrying out the treatment of the invention.

Referring now to FIG. 4, apparatus is shown which may be used to provide radio frequency glow discharge treatment to the surface of tubing or silicone rubber in other forms and configurations. It is adapted for a "batch treatment" procedure although it can be readily modified for a "flow through" treatment procedure as shown schematically in FIG. 5.

A complete RF system as shown for producing gas discharge will include a reactor vessel 40, a generator 42, an impedance matching network 44, means 46 for applying an RF field to reactor 50, means 48 such as a meter or meters for measuring the RF power supplied to the discharge, a vacuum pump 50 and a pressure gauge 52. A flow controller and flow meter 54 may be included between one or more gas suppliers 56-58.

RF generator 42 is preferably one of those commercially available and preferably operates at a frequency of 13.56 MHz. Coupling of the RF power from the output of the matching network 44 may be accomplished either inductively or capacitively to generate the discharge in reactor 40 whereby a length of the tubing 60 contained therein may be exposed to the glow discharge for surface treatment.

Plasma gases can be grouped as nonpolymer-forming and polymer-forming types. Typical gases used in nonpolymer forming discharges are hydrogen, helium, argon, nitrogen, ammonia, carbon dioxide and, in special cases, $C_2F_6$ which can exchange hydrogen and fluorine. Examples of polymer-forming gases are $C_2F_4$ $C_3F_6$, $C_2H_4C_2H_2$ $CH_4$.

Nitrogen, argon, helium, carbon dioxide, ammonia, oxygen, $C_2F_4$, $C_3F_6$, $C_2F_6$ and combinations thereof are preferred. Particularly preferred gases for use alone or in various mixtures are argon, oxygen, helium, nitrogen, ammonia and carbon dioxide, nitrogen being most particularly preferred.

Both nonpolymer-forming and polymer-forming plasma treatments of the surface of silicone rubber reduces surface blocking. The result is a reduction or elimination of stick/slip properties and a lower coefficient of friction. Plasma treatment with nonpolymer-forming gas is generally preferred.

As can be seen in FIG. 4, the gas or gas mixture is introduced into vacuum chamber reactor 40 which contains tubing 60 to be treated. The plasma electrodes 46, which may be inside or outside the reactor, are activated to produce the plasma glow discharge at a radio frequency of 13.56 MHz and at a wattage of from about 2 to 1000 watts, 2-250 watts being preferred. Typically, 50 watts is adequate and most preferred. Various treatment times and gas pressures may be used. Gas pressures may vary from about 0.01 to 1.0 Torr generally. With the preferred nitrogen gas, at a pressure of less than about 0.5 torr, for example 0.2-0.3 torr, and 50 watts, a treatment time of about 16 minutes is acceptable for silicone rubber tubing of about 0.068-0.101 inch OD.

Figure 5:
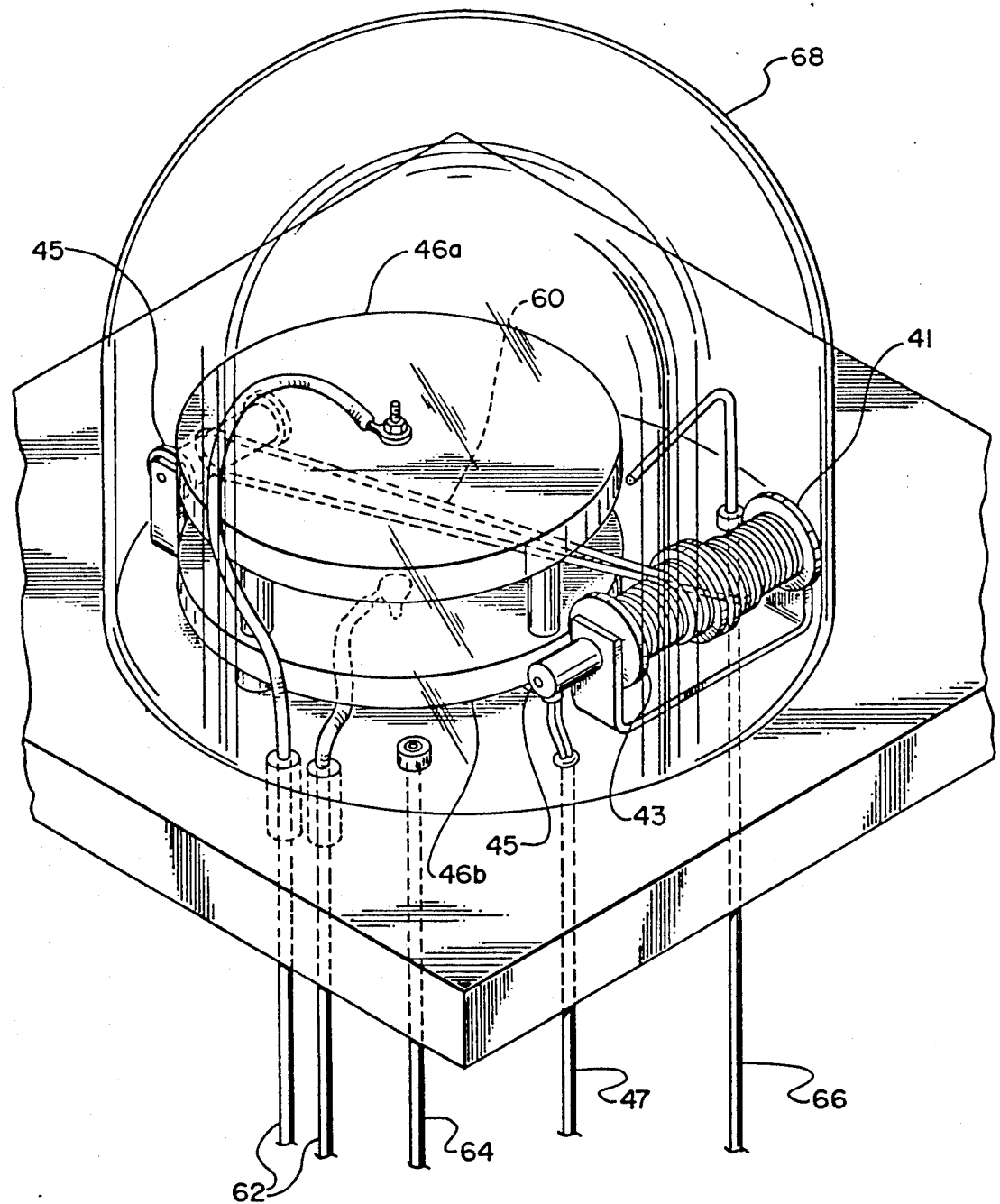
FIG. 5 shows schematically another apparatus for carrying out the treatment according to the invention.

Referring now to FIG. 5 and as already mentioned, apparatus for treating tubing on a "flow through" basis is shown. In this arrangement the tubing or other silicone rubber material is moved through the discharge region between anode 46a and cathode 46b as it is removed from a "take-off" reel 41 and rolled up on a "take-up" reel 43 which is operated electrically by a motor 45 and electrical lead 47. An idler pully 45 may be used for turnaround of the tubing. For example, a chamber as shown may be used to treat 100 foot rolls of tubing by winding it through at a speed adjusted to give the tubing a 16 minute exposure to the plasma. As the tubing is wound in the take-up reel 43, the speed at which the tubing travels through the plasma may increase. Monitoring and periodic changing of the tubing speed may be necessary.

The apparatus of FIG. 5 will additionally include electrical attachments 62, a vacuum conduit 64 and another conduit 66 for introducing gases into the closed environment defined by a bell jar 68 or the like.

Glow discharge treatment as described above has been found to improve silicone rubber surfaces without introducing residue or coating and with respect to "slip" and "blocking".

This completes the description of the preferred and alternate embodiments of the invention. Those skilled in the art may recognize other equivalents to the specific embodiment described herein which equivalents are intended to be encompassed by the claims attached hereto.

We claim:

1. An electrical lead for implantation having an outer covering of silicone rubber, the exterior surface of which is improved with respect to its surface characteristics by the treatment comprising exposure to radio frequency glow discharge in the presence of a gas at reduced pressure, said gas being selected from the group consisting of hydrogen, nitrogen, ammonia, oxygen, carbon dioxide, $C_2F_6$, $C_2F_4$, $C_3F_6$, $C_2H_4C_2H_2$, $CH_4$ and mixtures of any of the foregoing for a time sufficient to achieve the desired results.

2. The improvement of claim 1 wherein the glow discharge is in nitrogen.

3. The improvement of claim 2 when the glow discharge is at a radio frequency of 13.56 MHz.

4. The improvement of claim 3 wherein the discharge is from about 2 to 250 watts.

5. The improvement of claim 2 when the nitrogen is at a pressure of about 0.2 to 0.3 torr, the plasma voltage is about 50 watts and the treatment time is about 16 minutes.

6. In an electrical medical device adapted for interaction with a patient by means of a plurality of elongated electrical leads adapted for implantation in the patient's body, the leads including an outer covering substantially over their length comprised of silicone rubber, the improvement comprising treatment of the exterior surface of the silicone by exposing it to radio frequency glow discharge in the presence of a gas at reduced pressure, said gas being selected from the group consisting of hydrogen, nitrogen, ammonia, oxygen, carbon dioxide, $C_2F_6$, $C_2F_4$, $C_3F_6$, $C_2H_4C_2H_2$, $CH_4$ and mixtures of any of the foregoing for a time sufficient to achieve the desired results, whereby improved surface characteristics are provided.

7. The improvement of claim 6 wherein the gas is a mixture of nonpolymer forming gases.

8. The improvement of claim 6 wherein the glow discharge is in nitrogen.

9. The improvement of claim 8 when the glow discharge is at a radio frequency of 13.56 MHz.

10. The improvement of claim 9 wherein the discharge is at a wattage of from about 2 to 250 watts.

11. The improvement of claim 8 when the nitrogen is at a pressure of about 0.2 to 0.3 torr, the plasma voltage is about 50 watts and the treatment time is about 16 minutes.

12. Silicone rubber tubing for use as outer covering on implantable leads, the surface of which is treated by exposure to radio frequency glow discharge in the presence of a gas at reduced pressure, said gas being selected from the group consisting of hydrogen, nitrogen, ammonia, oxygen, carbon dioxide, $C_2F_6$, $C_2F_4$, $C_3F_6$, $C_2H_4C_2H_2$, $CH_4$ and mixtures of any of the foregoing for a time sufficient to achieve the desired results, whereby improved surface characteristics are provided.

13. The improvement of claim 12 wherein the gas pressure is between about 0.1 and 1.0 torr.

14. The tubing of claim 12 wherein the glow discharge is in nitrogen.

15. The tubing of claim 14 wherein the discharge is at a radio frequency of 13.56 MHz.

16. The tubing of claim 14 wherein the discharge is from about 2 to 250 watts.

17. The tubing of claim 14 wherein the nitrogen is at a pressure of about 0.2 to 0.3 torr, the discharge is at about 50 watts and the treatment time is about 16 minutes.

* * * * *

UNITED STATES PATENT AND TRADEMARK OFFICE
CERTIFICATE OF CORRECTION

PATENT NO. : 5,133,422
DATED : July 28, 1992
INVENTOR(S) : Arthur J. Coury et al.

It is certified that error appears in the above-indentified patent and that said Letters Patent is hereby corrected as shown below:

Column 4, line 48 of the patent, "$C_2H_4C_zH_z$" should be --$C_2H_4C_2H_2$--.

Column 5, line 2 of the patent, "$C_2H_4C_zH_z$" should be --$C_2H_4C_2H_2$--.

Signed and Sealed this

Thirteenth Day of September, 1994

BRUCE LEHMAN

Attest:

Attesting Officer

Commissioner of Patents and Trademarks